US008455227B2

(12) United States Patent
Rozmyslowicz et al.

(10) Patent No.: US 8,455,227 B2
(45) Date of Patent: Jun. 4, 2013

(54) DETECTION OF HIV-1 INFECTION

(75) Inventors: Tomasz Rozmyslowicz, Deptford, NJ (US); Krzysztof Wroblewski, Broomall, PA (US); Glen N. Gaulton, Havertown, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 847 days.

(21) Appl. No.: 11/922,404

(22) PCT Filed: Jun. 15, 2006

(86) PCT No.: PCT/US2006/023346
§ 371 (c)(1),
(2), (4) Date: Sep. 21, 2009

(87) PCT Pub. No.: WO2006/138481
PCT Pub. Date: Dec. 28, 2006

(65) Prior Publication Data
US 2010/0034747 A1    Feb. 11, 2010

Related U.S. Application Data

(60) Provisional application No. 60/690,489, filed on Jun. 15, 2005, provisional application No. 60/690,491, filed on Jun. 15, 2005.

(51) Int. Cl.
| | | |
|---|---|---|
| *C12N 13/00* | (2006.01) | |
| *G01N 33/00* | (2006.01) | |
| *G01N 33/48* | (2006.01) | |
| *G01N 21/62* | (2006.01) | |
| *G01N 24/00* | (2006.01) | |

(52) U.S. Cl.
USPC .......... 435/173.1; 436/63; 436/103; 436/105; 436/171; 436/173; 435/7.24

(58) Field of Classification Search
None
See application file for complete search history.

(56) References Cited

PUBLICATIONS

Lim AK et al "The relationship of in vivo 31P MR spectroscopy to histology in chronic hepatitis C". Hepatology. Apr. 2003;37(4):788-94.*
Bottomley PA et al. "AIDS dementia complex: brain high-energy phosphate metabolite deficits". Radiology. Aug. 1990;176(2):407-11.*
Chen K. "Study of Polyphosphate Metabolism in Intact Cells by 31-P Nuclear Magnetic Resonance Spectroscopy" Progress in Molecular and Subcellular Biology, vol. 23 H. C. Schroder, W. E. G. Miiller (Eds.) Springer-Verlag Berlin Heidelberg 1999; pp. 253-273.*
Thomas, et al. "Phosphorus metabolism during growth of lymphoma in mouse liver: a comparison of 31P magnetic resonance spectroscopy in vivo and in vitro*" Br. J. Cancer (1994) 69:633-640.*
Constantinidis et al. "31P-Nuclear Magnetic Resonance Studies of the Effect of Recombinant Human Interleukin la on the Bioenergetics of RIF-1 Tumorsl" Cancer Res. 49:6379-6382, 1999.*
Sappey-Marinier et al., "Alterations in brain phosphorus metabolite concentrations associated with areas of high signal intensity in white matter at MR imaging", Radiology, Apr. 1992; 183(1):247-56.
Leach et al., "Measurements of human breast cancer using magnetic resonance spectroscopy: a review of clinical measurements and a report of localized 31P measurements of response to treatment", NMR biomed 1998, 11: 314-340, 1998.
Wroblewski et al., "31-P NMR studies of HIV-infected human cells", Report No. 1951/AP: XXXVII Polish Seminar on Nuclear Magnetic Resonance and its Applications 2004, pp. 106-107.
International Search Report of Application No. PCT/US06/23346, issued on Jun. 4, 2008.
European Search Report of Application No. 06784934.9, issued on Apr. 7, 2010.

* cited by examiner

*Primary Examiner* — Louise Humphrey
(74) *Attorney, Agent, or Firm* — Mark S. Cohen; Pearl Cohen Zedek Latzer, LLP

(57) ABSTRACT

This invention provides methods for to the use of the difference in phosphodiester (PDE)/phosphomonoester (PME) ratio in biological fluids, as an analytical criterion to image both the presence and degree of viral infection in-vivo.

5 Claims, 6 Drawing Sheets

A

B

A

B

SEQUENCE LISTING

```
<160> NUMBER OF SEQ ID NOS: 2

<210> SEQ ID NO 1
<211> LENGTH: 22
<212> TYPE: DNA
<213> ORGANISM: Homo sapiens

<400> SEQUENCE: 1
acaagctagt acgagttgag cc                                                  22

<210> SEQ ID NO 2
<211> LENGTH: 23
<212> TYPE: DNA
```

```
-continued

<213> ORGANISM: Homo sapiens

<400> SEQUENCE: 2
cacacactac ttgaagcact tca                                              23
```

DETECTION OF HIV-1 INFECTION

CROSS REFERENCE TO RELATED APPLICATIONS

This application is a National Phase Application of PCT International Application No. PCT/US06/23346, International Filing Date 15 Jun. 2006, claiming priority from U.S. Provisional Patent Application No. 60/690,489, filed 15 Jun. 2005 and U.S. Provisional Patent Application No. 60/690,491, filed 15 Jun. 2005, all, which are incorporated herein by reference in their entirety.

FIELD OF INVENTION

This invention relates to methods for a reliable, specific and sensitive assay that is affordable and practical on a large scale, and has potential for in vivo imaging detection of HIV. More specifically, the invention relates to the use of alterations in cellular metabolites, as an analytical criterion to test the presence and degree of HIV infection.

BACKGROUND OF THE INVENTION

Human immunodeficiency virus (HIV) has been implicated as the primary cause of the degenerative disease of the immune system termed acquired immune deficiency syndrome (AIDS). Infection of the $CD4^+$ subclass of T-lymphocytes with the HIV type-1 virus (HIV-1) leads to depletion of this essential lymphocyte subclass which inevitably leads to opportunistic infections, neurological disease, neoplastic growth and eventual death.

Infection with human immunodeficiency virus (HIV) is a chronic process with persistent, high rates of viral replication. The pathogenesis of HIV-1 infection is characterized by a variable but often prolonged asymptomic period following the acute viremic phase.

Assays, which have been developed to detect the infection of HIV and monitor the progression of HIV in the body include inter-alia counting the depletion of CD4+ cells to indicate the prognosis of AIDS. In addition, serological screening techniques are also being utilized worldwide for the detection of HIV, where the presence of the antibody against HIV antigens, such as the HIV p24 antigen, is detected.

Other tests, like an ELISA assay or Polymerase Chain Reaction (PCR) to detect virus nucleic acids in serum samples, are currently being utilized to make the determination of the presence and degree of infection. However, these assays suffer from three primary defects: (1) They may not be sensitive enough to detect all HIV infected individuals, for example because some HIV infected individuals do not have detectable levels of serum antibody to HIV; (2) There may be a significant time lag between detection of HIV infection and either seroconversion or the production of significant amounts of virus circulating in the blood. In addition, some HIV infected but seronegative individuals might never convert but will remain infected throughout theirs lives. Other similar problems exist with the method for detecting HIV infection in seronegative individuals, described by Jehuda-Cohen, T. et al. (Proc. Natl. Acad. Sci. USA, 87: 3972-3076 (1990)) wherein peripheral blood mononuclear cells (PBMC) are isolated from the blood and then exposed to a mitogen such as pokeweed mitogen. In this instance incubation of isolated PBMC with pokeweed mitogen caused the PBMC to secret immunoglobulins that were specific for HIV; and lastly (3) Existing detection methods rely primarily on responses (antibody or virus levels) within the peripheral blood supply and do not detect or otherwise represent infection in the primary immune or other body organs: often these are the primary sites of HIV infection.

In sum, the failure of the ELISA, PCR and other existent assays to detect all HIV infected individuals places the population at risk by misleading HIV infected individuals with the diagnosis that they are not infected, thereby delaying the initiation of drug therapy and by making it more likely that the HIV infected individuals will unknowingly infect others. Similarly, reliance on infection assays that predict HIV presence in the peripheral blood, and not HIV infection at other primary internal infection sites within the body, may provide grossly misleading information on the whole body concentration of virus before and after drug therapy. For example, if selected drug therapies alter the shedding of virus into the blood the impact of therapy on actual virus infection may well be either overestimated or hidden by an artifactual picture of virus clearance from central reservoirs.

It is therefore evident that current methods employed for the detection of HIV-1 infection in humans, which are based on the production of HIV-1 antibodies, viral nucleic acid or gene products, do not permit direct, real-time measurement of HIV infection in vivo and thus may generate false negatives, which in turn may increases the probability of HIV infection of healthy people by infected individuals.

SUMMARY OF THE INVENTION

In one embodiment the invention provides a method for the detection of viral infection in a subject, comprising: obtaining a biological sample from said subject; analyzing said biological sample for an alteration in predetermined cellular metabolites; quantifying the alterations; and comparing said quantified alterations with a standard metabolite levels, wherein alteration in said predetermined metabolite levels relative to the standard metabolite levels, indicates viral infection in the subject.

In another embodiment, the invention provides a method for gauging the efficacy of an antiviral treatment in a subject, comprising: obtaining a biological sample from said subject; analyzing said biological sample for an alteration in the level of predetermined cellular metabolites; quantifying the alterations; comparing said quantified alterations with a standard metabolite levels; and monitoring the rate at which the predetermined metabolite level returns to the standard metabolites levels as a function of time, dose, pre-existing pathologies, environmental factors, type of medication, cocktail composition, side effects or combination thereof, wherein the faster the return of the altered metabolites level to the standard metabolite level, the more effective is the treatment.

In one embodiment, the invention provides a method for rational drug design for HIV-1 therapy, comprising: choosing a candidate compound; exposing an infected subject to said candidate compound; obtaining a biological sample from said infected subject; analyzing said biological sample for an alteration in the level of predetermined cellular metabolites; quantifying the alterations; comparing said quantified alterations with a standard metabolite levels; and monitoring the rate at which the predetermined metabolite level returns to the standard metabolites levels as a function of time, dose, pre-existing pathologies, environmental factors, type of medication, cocktail composition, side effects or combination thereof, wherein a return of the altered metabolites level to the standard metabolite level, indicates the drug is effective for HIV-1 therapy.

In another embodiment, the invention provides a method for classifying the severity of a viral infection in an infected subject, comprising: obtaining a biological sample from said subject; analyzing said biological sample for an alteration in predetermined cellular metabolites; quantifying the alterations; comparing said quantified alterations with a standard metabolite levels; and computing the difference between said observed ratio and a standard ratio, wherein the larger the difference between the computed levels and the standard's levels, the more severe is the infection.

In one embodiment, the invention provides a method for in-vivo imaging of the magnitude, location or their combination, of active or passive HIV infection in a subject comprising the step of: obtaining a full body or organ specific magnetic resonance imaging (MRI) or other similar scan from said subject, utilizing alterations in predetermined cellular metabolites as the primary evaluative criteria; and computing the difference between said observed image and a standard image taken from uninfected tissue or organ, wherein the larger the difference in the obtained image in a given tissue or organ location, the more severe is the infection in that location.

In another embodiment, the invention provides a method for rational drug design for HIV-1 therapy, comprising the steps of: choosing a candidate compound; exposing an infected organ or tissue to said candidate compound; obtaining a full body or organ specific magnetic resonance imaging (MRI) or other similar scan from said subject, utilizing alterations in predetermined cellular metabolites as the primary evaluative criteria; and computing the difference between said observed image and a standard image taken from uninfected tissue or organ; and monitoring the rate at which the obtained image returns to the standard image taken from uninfected tissue or organ as a function of time, dose, preexisting pathologies, environmental factors, type of medication, cocktail composition, side effects or combination thereof, wherein a return of the obtained image, to the standard image taken from uninfected tissue or organ, indicates the drug is effective for HIV-1 therapy.

DETAILED DESCRIPTION OF THE INVENTION

Figure 1:
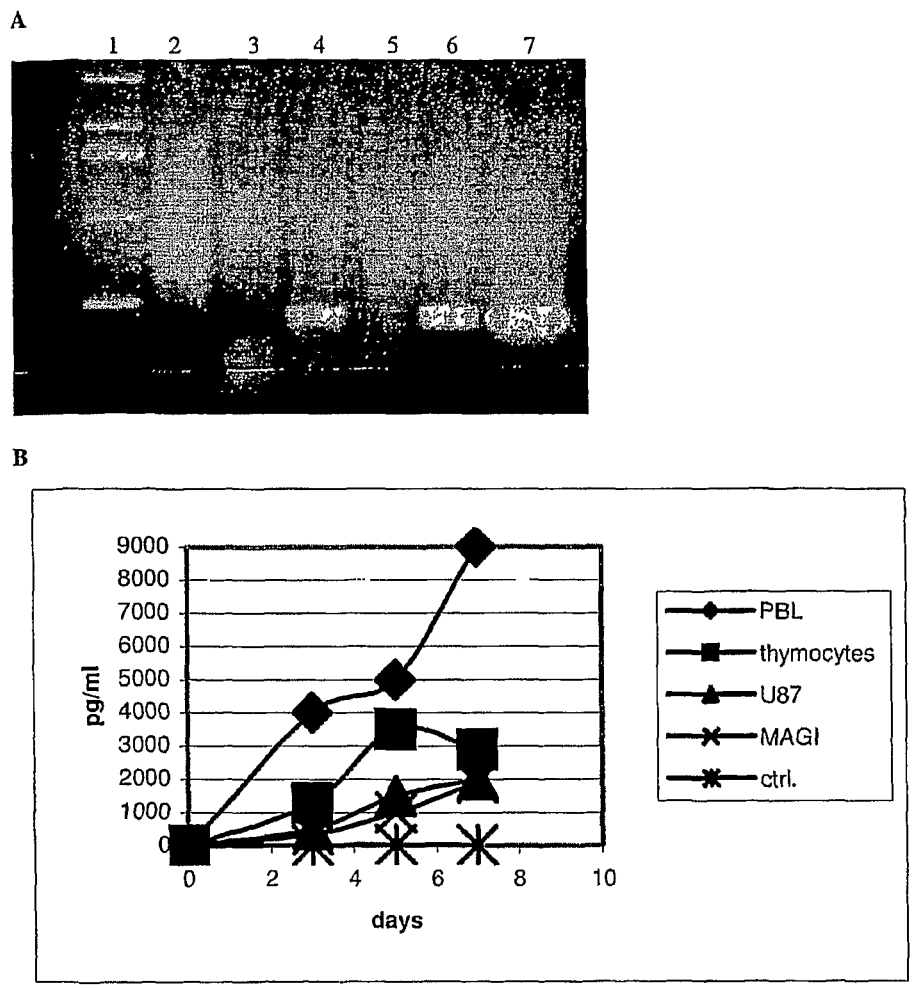
FIG. 1A shows PCR analysis of viral infection in human lymphocytes. 1B shows HIV-1 infection and replication in different human cells (ELISA analysis).

In one embodiment, the ability to dynamically image viral infections, such as HIV-1 in one embodiment, is an important advance in understanding and targeting viral reservoirs, such as in infections of the lymphoid organs, bone marrow, central nervous system (CNS), cardiac and renal tissues and organs, which are presently very difficult, if not impossible, to evaluate and control under real-time, in vivo conditions.

In one embodiment, viral reservoirs are a pool of latently infected cells in the resting CD4$^+$ T cell compartment. In another embodiment, viral reservoirs are virologically quiescent and are lacking the ability to produce multiply spliced RNA or viral particles. In another embodiment, low levels of ongoing viral replication continue to persist and consequently prolong the overall half-life of the virus. These viruses include in some embodiments, the persistence of replication-competent virus, unintegrated proviral DNA, both linear and circularized, and cell-associated RNA.

Current methods employed for the detection of viral infection are based in some embodiments on the production of virus-specific antibodies, or viral nucleic acid or gene products. However, none permit real-time measurement of the location and magnitude of infection in vivo. In view of the fact that in one embodiment, HIV-1 frequently establishes permissive infection of cells, described herein is the use of cellular metabolic changes related to the impact of virus infection and replication to detect the existence and severity of viral infection.

Therefore, according to this aspect of the invention and in one embodiment, the invention provides a method for the detection of viral infection in a subject, comprising: obtaining a biological sample from said subject; analyzing said biological sample for a concentration of phosphodiester (PDE) and a concentration of phosphomonoester (PME); computing an observed ratio of phosphodiester (PDE)/phosphomonoester (PME) from said concentrations; and comparing said observed ratio with a standard ratio, wherein reduction in the PDE/PME ratio indicates viral infection in the subject.

In another embodiment, provided herein is a method for the detection of HIV infection in a subject, comprising obtaining a biological sample from said subject, analyzing said biological sample for a concentration of phosphodiester (PDE) and a concentration of phosphomonoester (PME); computing an observed ratio of phosphodiester (PDE)/phosphomonoester (PME) from said concentrations; and comparing said observed ratio with a standard ratio.

In one embodiment, the viral infections for which detection according to the methods described herein are sought are human immunodeficiency virus (HIV), human hepatitis C virus (HCV), poliovirus, West Nile virus, foot and mouth disease virus or their combination.

In one embodiment, RNA viruses initiate RNA synthesis by de novo synthesis, wherein the process involves the active site of the polymerase, the initiation nucleotide (the NTPi) that provides the 3'-hydroxyl for nucleotidyl transfer to a second nucleoside triphosphate (NTP), and a template initiation site. The NTPi binds to the i site in the polymerase and is base paired to T1. The second NTP binds to the i+1 site and is paired with T2. Following the synthesis of the first phosphodiester bond, either the polymerase or the template translocates and the i+1 site is used to incorporate subsequent nucleotides. The initiated RNA can then be coupled to other processes, such as the addition of the 5' cap in another embodiment. De novo initiation is used by numerous RNA viruses, including in one embodiment, those with genomes of positive, negative, and ambisense strand RNA. Those include in one embodiment, the double-stranded RNA viruses, negative-strand RNA viruses, positive-stranded alphavirus-like viruses or their combination. In one embodiment, infection by viruses initiating de-novo infection, will result in synthesis of phosphodiesters, resulting in an increase in the ratio between PDE and PME and will be detected by the methods described herein.

In another embodiment concentration of phosphodiester (PDE) ratio, to upfield concentration of phosphomonoester (PME) in perchloric acid extracts of cells infected with HIV as measured by $^{31}$P NMR spectroscopy or in another embodiment, by any other analytical method (PDE/PME=0.39), is about 41% lower than in uninfected cells (PDE/PME=0.95), as shown in the FIGS. 3A and B. The relatively easy to measure difference in PDE/PME concentrations, is significant enough in one embodiment, to be used as an analytical criterion to describe the presence or degree of HIV infection. The methods disclosed in the embodiment described herein, provide a reliable, specific and sensitive test that is affordable and practical on a large scale, and has potential for in vivo imaging detection of HIV.

In one embodiment, the concentration of the various cellular metabolites and markers described herein, are measured in parts-per-million (ppm) obtained from calculating the area under the curve (AUC) of the spectroscopic method employed to determine the concentration of the cellular markers or metabolites. The area under the curve is the integral of a continuous, positive real-valued function $f$ of one real variable predetermined metabolite, between a left endpoint a, defined as the inflection point between the measured peak and the peak to the left of it; and a right endpoint b defined as the inflection point between the measured peak and the peak to the right of it, representing the area bounded by the lines x=a, x=b, the x-axis, and the curve defined by the graph of $f$.

In another embodiment, PDE/PME ratio in the biological samples used in the methods described herein is about 20-95% lower than in uninfected biological samples, or between about 25-75% lower, or between about 35-65% lower, or between about 40-55% lower, or between about 40-45% lower than in uninfected biological samples in other embodiments.

In one embodiment, the PDE/PME ratio in the infected biological samples is dependent on the detection method used, the type of virus whose infectivity is sought to be determined and the degree of infection. One skilled in the art would recognize that it is the difference between the infected PDE/PME ratio and the ratio of the uninfected control which determines the presence and severity of the viral infection. Accordingly, in one embodiment PDE/PME ratio in the infected biological sample is between about 0.7-0.3, or between about 0.7-0.2, or between about 0.6-0.3, or between about 0.5-0.4, or between about 0.4-0.3 in other embodiments.

NMR spectroscopy is employed in one embodiment, for the evaluation of functional changes in mammalian cells that are acutely affected by ischemia dementia, encephalopathy, epilepsy, malignant disease not located in the brain, multiple sclerosis, myocardial ischemia, Parkinson's disease, psychiatric disorders or inflammation in other embodiments, such as cardiomyocytes in another embodiment, or kidney epithelium in another embodiment. In one embodiment $^{31}$P-NMR enables the correlation of changes in the concentrations of intracellular metabolites or in another embodiment, of bioenergetic parameters that are key to mammalian cell functions. These include phosphocreatine (PCr) in one embodiment, or adenosinetriphosphate (ATP) in another embodiment, or inorganic phosphate (Pi) in another embodiment. While, in one embodiment $^{31}$P-NMR spectroscopy is noninvasive, the relatively low sensitivity of this technique in another embodiment, is a distinct disadvantage. There are several factors that contribute to low sensitivity. Among these are the polarization of atomic nuclei in one embodiment, or concentration in another embodiment, or the restricted rotation of atoms in membrane bilayers in another embodiment, or interactions with paramagnetic ions in another embodiment, or limited ability to maintain extended cell viability in observation chambers in another embodiment or combination of factors in another embodiment.

In another embodiment, the PDE/PME ratio is measured using $^1$H or $^{13}$C, magnetic resonance spectroscopy (MRS). In another embodiment, PDE/PME ratio is analyzed using any or all of the $^{31}$P, $^1$H or $^{13}$C isotopes, thereby obtaining increased sensitivity for the methods described herein.

Magnetic resonance imaging (MRI) refers in one embodiment to a multiplanar imaging method based on the interaction between radiofrequency electromagnetic fields and certain atomic nuclei in the body. In one embodiment, when different molecules vibrate at different frequencies when stimulated by a magnet, MRI has the ability detect these frequencies thereby being able to detect the measured components. In another embodiment, magnetic resonance spectroscopy (MRS) utilizes the principle that nuclei in different chemical structures have different characteristic resonance patterns, depending on the neighboring chemical structures and the interactions between these various chemical structures. MRS detects the chemical composition of the tissue under study, and the associated software displays a waveform with peaks that correspond to the various chemicals detected. In one embodiment, MRS allows visualization of molecular processes as opposed to structural and anatomic imaging of tissues and organs. In another embodiment, MRS provides direct biochemical information of cellular processes, such as viral infection and the subsequent changes in the PDE/PME ratio.

In order to remedy these limitations, perchloric acid (PCA) cell extracts are used in one embodiment for analysis instead of live cells. In another embodiment, PCA extraction preserves the cytosolic composition of cells, and is homogenous which improves resolution of the spectra and significantly increases sensitivity. In one embodiment extraction enables removal of existing paramagnetic impurities, or in another embodiment enables pH-adjusted extracts to be stable even during long NMR acquisitions. In another embodiment PCA extraction is used as a starting point for NMR analysis of HIV-1 infected cells. In one embodiment, changes in cellular metabolites serve as a reliable and sensitive diagnostic marker for HIV-1 infection.

In another embodiment, differences in the low field part of the $^{31}$P-NMR spectra of HIV-1 infected and uninfected cells are significant. HIV-1 infected cell lines display in one embodiment a 2-2.5-fold decrease in the ratio of PDE to PME. In one embodiment, this difference was observed in NMR spectra obtained from numerous human cell lines such as SupT1 in one embodiment, or CEM in another embodiment, or U87 in another embodiment or MAGI in another embodiment, and using in one embodiment X4 or X4/R5 tropic HIV-1 in another embodiment. HIV-1 infection in primary PBMC isolates infected either in vitro or obtained from HIV-1 infected patients, showed in one embodiment a similar change, but of slightly less magnitude (0.482 vs. 0.270).

NMR visible PME and PDE are involved in one embodiment, in biochemical or biophysical processes related to the synthesis and function cellular membranes. PME include in another embodiment phosphocholine (PC) and phosphoethanolamine (PE) while in another embodiment PDE was identified mainly as glycerophosphorylcholine and glycerophosphorylethanolamine. The presence of these metabolites is controlled in one embodiment, by the catabolic pathways of phospholipids, which in another embodiment, involve phospholipases or phosphodiesterases in another embodiment. In one embodiment, PC and PE are the precursors of phosphatitydlcholine and phosphatidylethanolamine, respectively.

In one embodiment, the viral infection is of a lentivirus. The lentivirus group can be split into "primate" and "non-primate". In one embodiment, primate lentiviruses include human immunodeficiency virus (HIV), the causative agent of human auto-immunodeficiency syndrome (AIDS), and simian immunodeficiency virus (SIV). The non-primate lentiviral group includes in another embodiment, the prototype "slow virus" visna/maedi virus (VMV), as well as the related caprine arthritis-encephalitis virus (CAEV), equine infectious anaemia virus (EIAV) and feline immunodeficiency virus (FIV) and bovine immunodeficiency virus (BIV).

The lentivirus HIV-1 is comprised in one embodiment, of an RNA genome encapsulated in a lipid bilayer Both HIV-1 entry in one embodiment, or replication in another embodiment, occur by fusion with the outer plasma membrane of cells. Budding of HIV-1 particles during virus replication alters in another embodiment, the composition of the plasma membrane. This is seen in another embodiment, in several plus-strand RNA virus infections, or in another embodiment in human hepatitis C virus (HCV), or poliovirus in another embodiment, or West Nile virus in another embodiment, or foot and mouth disease virus in another embodiment. In one embodiment, changes in the composition of cellular macromolecules, as evidenced by $^1$H-NMR signals of plasma membrane triglyceride pools, are observed for CD4+ lymphoblastoid cells in the early stages (30 minutes-8 days) after HIV-1 infection. In this instance the proton spectra in HIV-1 infected lymphoblastoid and promonocytic cells displayed a lower intensity of lipid signals.

Therefore, according to this aspect of the invention and in one embodiment, the invention provides a method for the detection of HIV infection in a subject, comprising obtaining a biological sample from said subject; analyzing said biological sample for a concentration of phosphodiester (PDE) and a concentration of phosphomonoester (PME); computing an observed ratio of phosphodiester (PDE)/phosphomonoester (PME) from said concentrations; and comparing said observed ratio with a standard ratio, wherein said biological sample is serum in one embodiment, or plasma in another embodiment, or saliva in another embodiment, or urine in another embodiment, or blood cell lysate in another embodiment, or lymphatic fluids in another embodiment, or lymphocytes in another embodiment, or peripheral blood mononuclear cells (PBMC) in another embodiment, or thymocytes in another embodiment or combination thereof. In another embodiment, biological fluids as described hereinabove are used in the methods and embodiments of the invention described herein.

In one embodiment, the term "lysate" or "blood cell lysate" refers to the cellular debris, such as membrane fractions, organelles and the like and fluid produced by the process of lysis, which in one embodiment, may be enzymatic, or in another embodiment, chemical or in another embodiment thermal.

In another embodiment, the term "peripheral blood mononuclear cells" or "(PMBC)" refers to HIV qualitative culture utilizing a patient's peripheral blood mononuclear cells which are in one embodiment lymphocytes or in another embodiment monocytes, in co-culture with HIV seronegative donor PBMCs.

In one embodiment, the PDE/PME ratio in infected biological sample are compared to a non-infected control, which in another embodiment is taken from a subject whom is seronegative to the viral infection assayed. The term "seronegative" refers to a serum lacking an antibody of a specific type or in another embodiment, refers to the absence of prior infection with a specific agent such as, in one embodiment, the HIV-1 virus, or in another embodiment, the disappearance of antibodies after treatment of a disease or in another embodiment, absence of antibody usually found in a given syndrome such as AIDS in another embodiment. In one embodiment, the term "control" refers to a subject or pool of subject that are not infected, are seronegative to the virus, have been infected and treated successfully, showing no traces of the virus for a period of no less than a year, or in another embodiment, a combination of subjects or pool of subjects as described herein.

In another embodiment, the expression of cellular markers are compared to a control, which in another embodiment is taken from a subject whom is seropositive to infection with HIV-1. In one embodiment, the term seropositive refers to an individual whose serotype suggests that they have experienced infection in the past. In one embodiment, the cellular markers used in the methods described herein.

In one embodiment, the standard used for the purposes of comparison in the methods described herein, is taken from a subject or pool of subject before treatment, or in other embodiment, after treatment, or in another embodiment, during treatment. In one embodiment, the standard used in the methods described herein, for the purpose of determining the degree of difference between the obtained values of the cellular marker used, and the standard values, is an industry standard. In one embodiment, an industry standard for uninfected is used as the standard control for comparison purposes.

In one embodiment, the term "cellular marker" refers to any somatic or genetic marker of a cell that is detectable and/or measurable. A cell may be determined to be positive or negative for any selected cellular marker providing that there is a corresponding probe that binds to the marker. Further, quantifying and/or measuring the intensity of each marker of interest is an embodiment of the invention. Biological and molecular characterization may involve characterizing single macrophage based on antibody binding activity to an antigen (e.g., receptor, intracellular protein and/or peptide) to measure proliferative and infectivity activities, for example. In another embodiment, the cellular markers used in the methods described herein are inorganic phosphate (Pi), phosphocholine (PC), phosphoethanolamine (PE), glycerophosphorylcholine (GPC), glycerophosphorylethanolamine (GPE). The presence of these markers is controlled in one embodiment, by the catabolic pathways of phospholipids, which involve phospholipases as well as phosphodiesterases. PC and PE are the precursors of phosphatitydlcholine and phosphatidylethanolamine, respectively.

"lymphocytes" or "cells" are non-antibody producing lymphocytes that constitute a part of the cell-mediated arm of the immune system. T cells arise in one embodiment from immature lymphocytes that migrate from the bone marrow to the thymus, where they undergo a maturation process under the direction of thymic hormones. Here, the mature lymphocytes rapidly divide increasing to very large numbers. The maturing T cells become immunocompetent based on their ability to recognize and bind a specific antigen. Activation of immunocompetent T cells is triggered when an antigen binds to the lymphocyte's surface receptors.

In one embodiment, if the patients cells contain HIV, the viral particles will be released into the culture and will infect the donor cells and propagate the virus. In another embodiment, at various intervals during the culture, the media is tested for the presence of p24 Ag (HIV core protein), which in one embodiment, indicates peak viral production. In another embodiment, positive cultures are terminated at any point during the culture, but negative culture in one embodiment, or indeterminate cultures in another embodiment, are terminated by day 28-31. The viral isolates from positive cultures are used in one embodiment, for studies including genotypic or phenotypic analyses. In another embodiment, the cultured cells are used to analyze proviral DNA.

In one embodiment, peripheral blood mononuclear cells (PBMCs) are obtained from ACD, or in another embodiment, from EDTA-treated blood, or Heparin in another embodiment, or citrate-anticoagulated whole blood in another embodiment. In one embodiment, for molecular studies, including in one embodiment plasma viral load, EDTA is used. In one embodiment PMBC's obtained will vary from subject to subject.

In one embodiment, the invention provides a method for the detection of HIV infection in a subject, comprising obtaining a biological sample from said subject, analyzing said biological sample for a concentration of phosphodiester (PDE) and a concentration of phosphomonoester (PME); computing an observed ratio of phosphodiester (PDE)/phosphomonoester (PME) from said concentrations, wherein analyzing said observed ratio of phosphodiester (PDE)/phosphomonoester (PME) in said biological sample is done using RIA, ELISA, NMR, HPLC, GC, MS or combination thereof.

In another embodiment, other, much more sensitive technologies than NMR such as in one embodiment high-performance liquid chromatography (HPLC) or in another embodiment mass-spectrometry (MS) are used in order to determine PDE/PME ratio. In one embodiment, liquid chromatography-mass spectrometry is used, wherein PDE/PME ratio is determined by separating PDE alone in a known volume of PMBC's from a subject, followed by direct elution into a mass spectrometer. (LC-MS). In one embodiment, the process of sample preparation and measurement is automated to continuously analyse samples of biological fluids as described herein. In another embodiment, the ratio of two concentrations of PDE and PME is self-calibrated, or, in another embodiment, does not require any external standards, and in one embodiment, can be used directly to determine cell infection.

In one embodiment, noninvasive NMR measurement of phosphorus metabolites provides functional information and, in another embodiment, is used in quantification of HIV-1 induced disease. In one embodiment, significant and reproducible differences exist in the $^{31}$P-NMR spectra of HIV-1 infected and uninfected cells.

Figure 6:
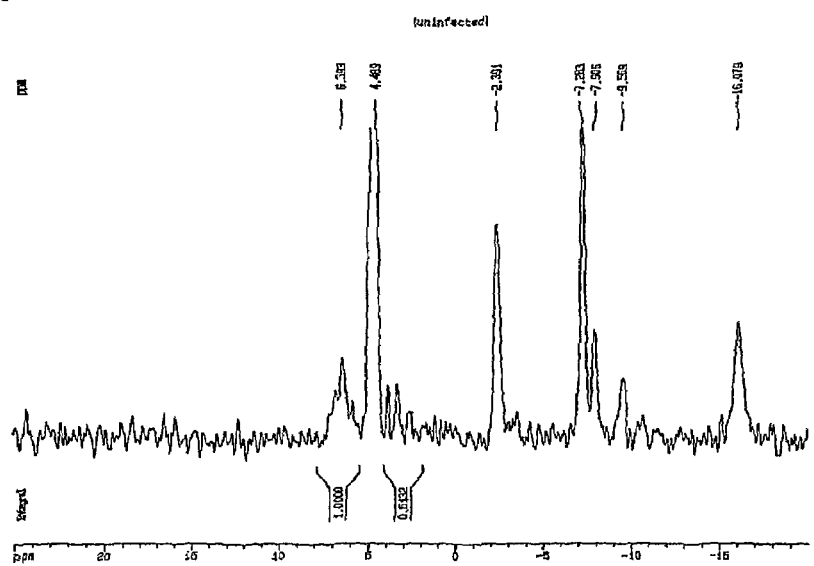
FIG. 6 shows $^{31}$P NMR spectrum of uninfected (A) and infected (B) intact human lymphocytes.
Figure 6:
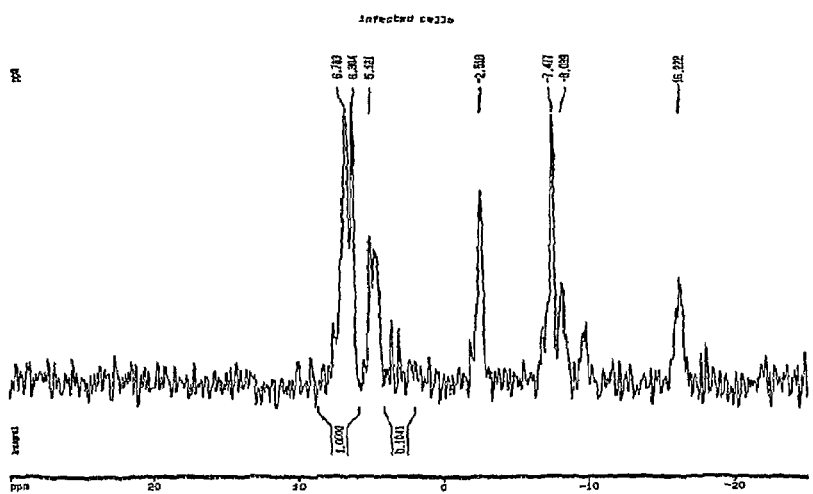

In one embodiment, and as shown in FIG. 6, the mean PDE/PME ratio for uninfected PBMC samples is 0.482±0.094. In another embodiment, the mean PDE/PME ratio for in vitro infected PBMC was 0.203±0.076. In one embodiment, the PDE/PME ratio for infected samples fell below the 0.482 mean PDE/PME ratio seen for uninfected lymphocytes. In one embodiment, $^{31}$P-NMR spectra of PBMC isolates produce mean PDE/PME ratio of 0.270±0.07, well below 0.482.

In another embodiment, the invention provides a method for the detection of HIV infection in a subject, comprising obtaining a biological sample from said subject, analyzing said biological sample for a concentration of phosphodiester (PDE) and a concentration of phosphomonoester (PME); computing an observed ratio of phosphodiester (PDE)/phosphomonoester (PME) from said concentrations; and comparing said observed ratio with a standard ratio, wherein said observed ratio is lower than about 0.482, thereby indicating said subject is infected with HIV-1, or in another embodiment said observed ratio is higher than about 0.482, thereby indicating said subject is uninfected with HIV-1

In another embodiment, difference between uninfected and HIV-1 infected cells when measured by $^{31}$P-NMR in vitro is large enough to serve as a reliable detection method of in vivo HIV-1 infection. In one embodiment, the methods of the invention described herein, rapidly measure the degree of infection within isolated cell populations. This might be accomplished using either NMR, or perhaps in a more sensitive and time efficient manner, by HPLC or MS technologies, which can be easily automated. The potential longer-term benefit of NMR analysis is in the development of noninvasive in vivo imaging of HIV infection within the central nervous system or other tissues, which are not currently accessible to dynamic measurement. The ability to image HIV-1 infection in this manner is in one embodiment, a major step towards diagnosis or, in another embodiment, treatment of HIV-infected patients.

Therefore, according to this aspect of the invention and in one embodiment, the invention provides a method for gauging the efficacy of HIV treatment in a subject, comprising obtaining a biological sample from said subject; analyzing said biological sample for a concentration of phosphodiester (PDE) and a concentration of phosphomonoester (PME); computing an observed ratio of phosphodiester (PDE)/phosphomonoester (PME) from said concentrations; and monitoring the rate of reduction in said observed ratio as a function of time in one embodiment, or dose in another embodiment, or pre-existing pathologies in another embodiment, or environmental factors in another embodiment, or type of medication in another embodiment, or cocktail composition in another embodiment or combination thereof in another embodiment.

In another embodiment, the invention provides a method for gauging the efficacy of HIV treatment in a subject, comprising obtaining a biological sample from said subject; analyzing said biological sample for a concentration of phosphodiester (PDE) and a concentration of phosphomonoester (PME); computing an observed ratio of phosphodiester (PDE)/phosphomonoester (PME) from said concentrations; and monitoring the rate of reduction in said ratio as a function of time in one embodiment, or dose in another embodiment, or pre-existing pathologies in another embodiment, or environmental factors in another embodiment, or type of medication in another embodiment, or cocktail composition in another embodiment or combination thereof in another embodiment, wherein an effective treatment is in one embodiment, that treatment reducing said observed phosphodiester (PDE)/phosphomonoester (PME) ratio to below about 0.482.

In one embodiment, the invention the invention provides a method a method for rational drug design for HIV-1 therapy, comprising choosing a candidate compound: exposing an infected subject to said candidate compound; obtaining a biological sample from said infected subject; analyzing said biological sample for a concentration of phosphodiester (PDE) and a concentration of phosphomonoester (PME); computing an observed ratio of phosphodiester (PDE)/phosphomonoester (PME) from said concentrations; and monitoring the rate of reduction in said observed ratio as a function of time in one embodiment, or dose in another embodiment, or pre-existing pathologies in another embodiment, or environmental factors in another embodiment or a combination thereof in another embodiment.

In one embodiment, computer modeling allows the selection of a finite number of rational chemical modifications, as opposed to the countless number of essentially random chemical modifications that could be made, any one of which might lead to a useful drug. Each chemical modification requires additional chemical steps, which while being reasonable for the synthesis of a finite number of compounds, may become overwhelming if all possible modifications are needed to be synthesized. Thus through the use of a three-dimensional structural analysis and computer modeling, a large number of these compounds can be rapidly screened on the computer monitor screen, and a few likely candidates can be determined without the laborious synthesis of numerous compounds.

Once a potential drug or antagonist is identified, in one embodiment it either can be selected from a library of chemicals that are commercially available from most large chemical companies including Merck, Glaxo Welcome, Bristol Meyers Squib, Monsanto/Searle, Eli Lilly, Novartis and Pharmacia UpJohn, or in another embodiment the potential drug may be synthesized de novo. As mentioned herein, the de novo synthesis of one or even a relatively small group of specific compounds is reasonable experimentation for rational drug design.

RDD has been revolutionized by the introduction of high throughput synthesis and combinatorial chemistry which afford collections and mixtures of large numbers of synthetic compounds for the purpose of screening for biological activity. Such large mixtures and pools of compounds pose significant challenges for the bioassay and analytical scientist. The analytical challenge is two-fold: separation of the active component of a mixture, and the identification of its structure. A variety of separation methods are available, including LC, HPLC, and CE. However, from the standpoint of separating biologically active components from a mixture of one or more targets with a combinatorial library necessitates the use and development of methods that select for and separate the complex (usually noncovalent) between the ligands and the target. Affinity column methods may be used in certain embodiments to selectively isolate and subsequently analyze binding components of mixtures of compound.

In another embodiment, the ability of HIV-1 to regulate expression of cytokines and a cytokines coreceptors, or their function is used for rational drug design (RDD) described herein. In one embodiment, RDD includes not only knowing or predicting the conformation of a desired protein, but also being able to control and predict the conformation of a drug that is to interact with the target protein, such as a protein expressed on HIV-1 Env. In one embodiment, cellular metabolites include cytokines and their co-receptors.

In another embodiment, the invention provides a method for classifying the severity of an HIV-1 infection in an infected subject, comprising obtaining a biological sample from said subject; analyzing an observed ratio of phosphodiester (PDE)/phosphomonoester (PME) in said biological sample; and computing the difference between said observed ratio and a standard ratio. In one embodiment the standard ratio is 0.482 and in another embodiment, the larger the difference between said observed ratio and said standard ratio, the more severe is the HIV-1 infection.

In one embodiment, the invention provides a method for identifying the location of an HIV-1 infection in an infected or HIV exposed individual, comprising in vivo imaging of the magnitude of active and/or passive HIV infection within a human or animal subject: obtaining a full body or organ specific magnetic resonance imaging (MRI) or other similar scan utilizing alterations in cellular metabolites as the primary evaluative criteria; for example the concentration of phosphodiester (PDE) and/or phosphomonoester (PME) relative to other membrane lipids; computing an observed ratio of phosphodiester (PDE) and/or phosphomonoester (PME) relative to other lipids; and computing the difference between said observed ratios and a standard ratio in uninfected tissues, wherein the larger the greater the alteration in phospholipid metabolism, the more severe is the infection.

In another embodiment, the invention provides a method for classifying the severity of an HIV-1 infection in an infected or exposed subject, compromising in vivo imaging of the magnitude of active and/or passive HIV infection within a human or animal subject: obtaining a full body or organ specific magnetic resonance imaging (MRI) or other similar scan utilizing alterations in cellular metabolites as the primary evaluative criteria; for example the concentration of phosphodiester (PDE) and/or phosphomonoester (PME) relative to other membrane lipids; computing an observed ratio of phosphodiester (PDE) and/or phosphomonoester (PME) relative to other lipids; and computing the difference between said observed ratios and a standard ratio in uninfected tissues, wherein the larger the greater the alteration in phospholipid metabolism, the more severe is the infection.

In another embodiment, the invention provides a method for rational drug design for HIV-1 therapy, comprising: choosing a candidate compound; exposing an infected subject to said candidate compound; in vivo imaging of the effectiveness of said HIV therapy within an HIV infected human or animal subject by obtaining a full body or organ specific MRI or other similar scan utilizing alterations in cellular metabolites as the primary diagnostic criteria; for example the concentration of phosphodiester (PDE) and/or phosphomonoester (PME) relative to other membrane lipids; computing an observed ratio of phosphodiester (PDE) and/or phosphomonoester (PME) relative to other lipids; and monitoring the rate of reduction in said observed metabolic change as a function of time, dose, pre-existing pathologies, environmental factors, side effects or an optimized combination thereof to a phospholipid level of a seronegative subject, wherein a decrease in the phospholipid metabolic effects induced by HIV infection indicates the treatment is effective.

As used herein, "treatment" refers in one embodiment to any of (i) the prevention of infection or reinfection, as in a traditional vaccine, or (ii) the reduction or elimination of symptoms, and (iii) the substantial or complete elimination of the virus in question. Treatment may be effected prophylactically (prior to infection) or therapeutically (following infection) in other embodiments.

In one embodiment, the term "about" refers to a deviation from the range of 1-20%, or in another embodiment, of 1-10%, or in another embodiment of 1-5%, or in another embodiment, of 5-10%, or in another embodiment, of 10-20%.

The term "subject" refers in one embodiment to a mammal including a human in need of therapy for, or susceptible to, a condition or its sequelae. The subject may include monkeys, dogs, cats, pigs, cows, sheep, goats, horses, rats, and mice and humans. The term "subject" does not exclude an individual that is normal in all respects.

The following examples are presented in order to more fully illustrate the preferred embodiments of the invention. They should in no way be construed, however, as limiting the broad scope of the invention

EXAMPLES

Example 1

Detection of HIV-1 Infection, Using $^{31}$P NMR Spectroscopy

Materials and Methods
Cell Isolation and Tissue Culture

Cell lines. The human lymphocyte derived lines SupT1 and CEM employed were maintained in RPMI medium (Gibco-BRL, Grand Island, N.Y.) supplemented with 10% bovine calf serum (BCS) (Hyclone, Logan, Utah, USA). U87/CD4+ cells were maintained in DMEM medium (Gibco BRL) supplemented with 10% bovine calf serum (BCS) and geniticin (Gibco BRL) at a concentration of 0.2 mg/mL. MAGI/CD4+ cells were maintained in DMEM with geniticin and hygromycin B (RocheBMB, Indianapolis, Ind., USA) at a concentration of 0.1 mg/mL.

Human lymphocytes. Fresh, human peripheral blood mononuclear cells (PBMC) were obtained from uninfected donors as "buffy coat" To separate erythrocytes, cells were sedimented on 6% HES (Hespan) (B. Braun Med. Inc. Irvine, Calif., USA). Subsequently lymphocytes were isolated with Ficoll, placed in standard 75 cm$^2$ flasks (Falcon, BD, Franklin Lakes, N.J., USA) and maintained with RPMI medium supplemented as described above.

HIV-1 infected lymphocytes were isolated from 16 subjects. These individuals constitute both HIV-1 infected asymptomatic and AIDS patients, and were previously untreated by any regimen for HIV-1 infection. This population was restricted to individuals aged 18-50 and consisted of ~50% male, of which 100% were Black. Cells were isolated from these patients using the Ficoll procedure described above, then frozen with 10% DMSO supplemented with 90% of FBS. Cells were evaluated for viability in trypan blue and extracted with PCA. Only those samples with viability greater than 50% were utilized in subsequent studies.

Human thymocytes. Fresh neonatal thymic tissue, obtained from routine thoracic surgery (1 day-6 month old) was cut into 3 to 10 mm fragments and digested with 0.1% collagenase (Sigma, St. Louis, Mo.) and DNAase 10 IU/ml (Sigma) solution in Dulbecco's Phosphate-Buffered Saline (PBS) without calcium chloride and magnesium chloride (GibcoBRL, Gaithersburg, Md.) for 2 hours at 37° C. The fragments were subsequently passed through a 100 µm nylon cell strainer (Becton Dickinson, Franklin Lakes, N.J.), and washed. Mononuclear cells were isolated with Ficoll-Hypaque (Amersham Pharmacia, Uppsala, Sweden). Non-adherent cells (thymocytes) were collected, washed and incubated in RPMI medium (GibcoBRL) supplemented with 10-20% fetal bovine serum (FBS), 2 mM glutamine, 100 IU/ml of penicillin, 100 µg/ml of streptomycin and 0.25 µg/ml of amphotericin B.

DNA Isolation and PCR

Cells were maintained in 24-well plates (3×10$^4$ cells/well) prior to extraction. To collect DNA, 20 µl of Proteinase K was pipeted into the bottom of each well after removal of media. Then 200 µl of PBS was mixed with the cells, followed by the addition of 200 µl of lysis buffer. This mixture was heat inactivated for 2 hours at 60°. Samples were subsequently boiled for 15 minutes and DNA was purified as per the blood and body fluid protocol of the Qiamp DNA Blood Mini Kit (Qiagen, Valencia, Calif.). A 10 µl aliquot of each purified DNA sample was used as a template for PCR under the following conditions: 1×PCR Buffer, 1.5 mM MgCl$_2$, 15 mM dNTP, 1×Q reagent, 6 µM LTR-plus primer, 6 µM LTR-minus primer. After denaturing at 97° for 10 minutes, 0.6 µl of Taq Polymerase was added to each sample, and the PCR reaction was carried out under the following cycling parameters—30 seconds at 94°, 2 minutes at 55°, and 1 minute at 72°. This cycle was repeated 42 times, followed by a 10 minute 72° extension, to yield a product of 430 base pairs. All PCR reagents were obtained from Qiagen (Valencia, Calif.). HIV-1 primer sequences LTR: 5'-ACAAGCTAGTACGAGT-TGAGCC-3' (SEQ ID NO. 1) and HIV-1 primer sequence; 5'-CACACACTACTTGAAGCACTTCA-3' (SEQ ID NO. 2), were obtained. A 10 µl of product of reaction was run on a 1% agarose gel and visualized with 10 µg/ml ethidium bromide.

Infection with HIV-1

Human glioma cells (MAGI and U87) were maintained for one week in culture and then incubated with 89.6 or IIIB viral stocks at a concentration of 10 ng/ml. After a 12 hour incubation with virus, cells were washed 5 times with PBS solution, and maintained for the next 3-5 days in RPMI medium with 10% FBS. Cells were detached with trypsin and prior to PCA extraction. Lymphocytes were incubated with IIIB virus at 50 ng/ml for 12 hours. Cells were then washed to remove virus and incubated for 14 days. To confirm infection and viral replication, the p24 ELISA was used. P24 ELISA reactions were performed using Alliance HIV-1 p-24 ELISA kit (PerkinElmer, Boston, Mass.). Briefly, cell culture supernatant, serum or cell suspensions were placed in different dilutions in 96-well ELISA plate with TritonX-100 and incubated for two hours at 37° C. Following intensive washing and adding Detector Antibody plate was incubated for one hour again at 37° C. Subsequently the experimental samples were incubated with Streptavidin-HRP for 30 minutes at room temperature, treated with OPD Substrate Solution and read at 492 nm in the Plate Reader MRX Revelation (Dynex, Chantilly, Va.). The final viral concentrations were evaluated on a G4 Macintosh computer using Microsoft Excel 2000.

PCA Extraction, Live Cells NMR, NMR Data Acquisition and Processing

Cell pellets were placed on ice and extracted with PCA according to Askenazy et al. Askenazy N., Kushnir N., Navon G., Kaplan O. NMR in Biomedicine 3: 220-226 (1990). Subsequently KHCO$_3$ neutralized extract was lyophilized using a standard Speedvac unit connected to a high vacuum pump. The liophilizate was dissolved in 2 ml of D$_2$O. The pH of the sample was adjusted to 6.8 using 1 n HCl.

$^{31}$P NMR spectra of live cells (uninfected and 100% infected cells) were obtained. 10$^6$-5×10$^8$ cells were used (for each experiment) depending on their size. Measured signal areas were corrected for the incomplete relaxation during the repetition time. Cells (infected and uninfected) were handled at temperature not exceeding 4° C. Cooled down cells were placed in 10 mm teflon NMR tubes from Wilmad (Buena, N.J., USA), sealed, placed on ice, and transferred to the NMR Center for 1 hour analysis. Cell viability were assessed before and after each experiment. All phosphorus spectra were obtained at the temperature of 4° C.

All spectra were obtained on a Bruker AMX-500 NMR spectrometer at the phosphorus resonance frequency 202.46 MHz using 10 mm selective phosphorus probe with deuterium lock and proton decoupling, and processed with standard Bruker software (XWIN-NMR) on a Silicon Graphics workstation. A standard ID phosphorus spectrum with broadband proton decoupling was acquired using 25 degree acquisition pulse and 0.1 s relaxation delay. The temperature of the sample was stabilized at 298K. Obtained FID was processed using Gaussian/exponential line broadening (LB=−20 Hz, GB=0.02 Hz). Areas of PME and PDE signals were measured after Gaussian/Lorenzian curve fitting to the experimental data. Obtained values were corrected for the small amount of signal saturation using equation provided by Hsiech et al. (Hsiech, P. S. & Balaban, R. S. (1987) *J. Magn. Reson.* 74, 574-579), and spin-lattice relaxation times of PME and PDE by Okunieff et al. (Okunieff, P., Vaupel, P., Sedlacek, R. & Neuringer, L. J. (1989) *Int. J. Radiation Oncology Biol. Phys.* 16, 1493-1500).

Statistical Analysis:

Arithmetic means, standard deviations and p24 ELISA calculations were performed on a G4 Macintosh computer using Microsoft Excel 2000. Data was analyzed using the Student t-test for unpaired samples. Statistical significance was defined as p<0.05.

Results

The possibility that HIV-1 infected cells display an altered $^{31}$P-NMR spectra an initial analysis of cell lines infected in vitro with HIV-1 was tested. A number of established cell lines (U87, MAGI, SupT1 and CEM) and primary lymphocytes (PBMC and thymocytes), were first incubated a with HIV-1 (IIIB or 89.6) at an M.O.I.=0.01. Infection of these cells was confirmed by PCR and ELISA analysis after 12 hours. The PCR products of a representative panel of these cells is shown in FIG. 1A. An HIV-1 specific PCR product was detected at 474 bp for each cell type exposed to HIV-1, but not in uninfected cell cultures. Results of ELISA analysis for p24 gag expression conducted on similar cell populations, shown in FIG. 1B, confirm the infection of these cell lines by HIV-1.

Figure 2:
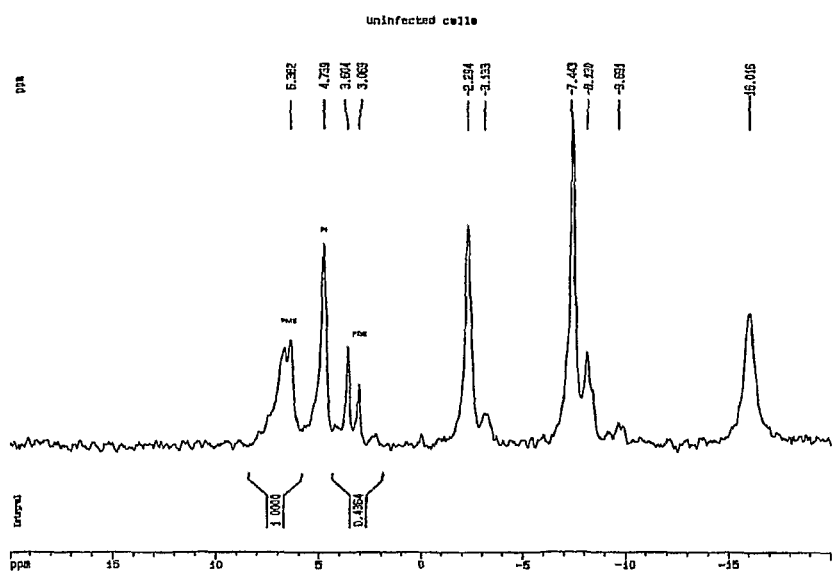
FIG. 2 shows $^{31}$P NMR spectrum of perchloric acid (PCA) extracts of HIV-1 in-vitro uninfected (A) and infected (B) human lymphocytes.
Figure 2:
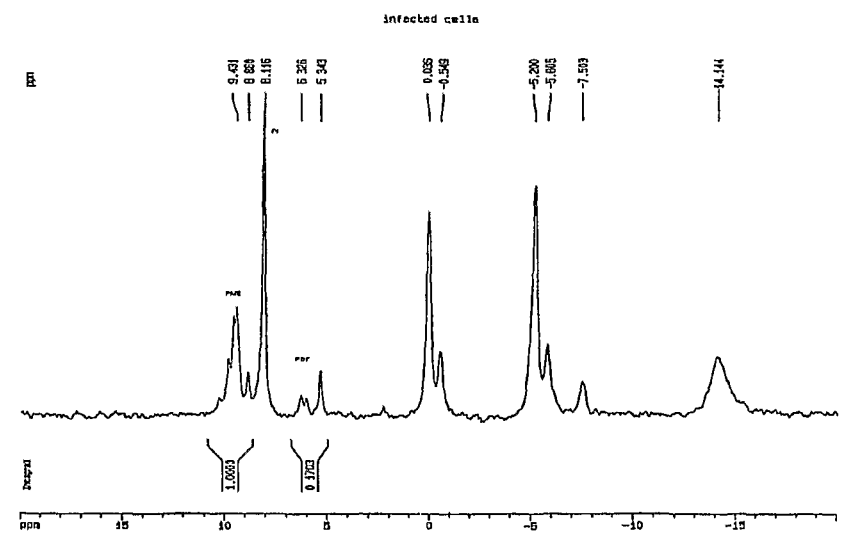

The $^{31}$P-NMR spectra of both infected and uninfected cells were then analyzed following PCA extraction, as described in the Experimental Design. The full $^{31}$P-NMR spectra of infected and uninfected PBMC extracts are shown in FIG. 2. Similar results were obtained with human thymocyte extracts and intact humane lymphocytes (FIG. 6). Both populations of PBMC displayed a relatively high level of phospholipid-associated phosphomonoesters (PME), such as phosphocholine ($\delta$=4.89 ppm) and phosphoethanolamine ($\delta$=5.07 ppm). The level of PME relative to inorganic phosphate (Pi) was found to be 3:1 in both samples. The most prominent difference between uninfected and infected cells was found in the phosphodiester (PDE) region ($\delta$=3.7 ppm), which contains predominantly phosphorylethanolamine and phosphorylcholine. The level of phosphodiesters relative to inorganic phosphate was approximately two times lower in infected cells than in the uninfected control.

Figure 3:
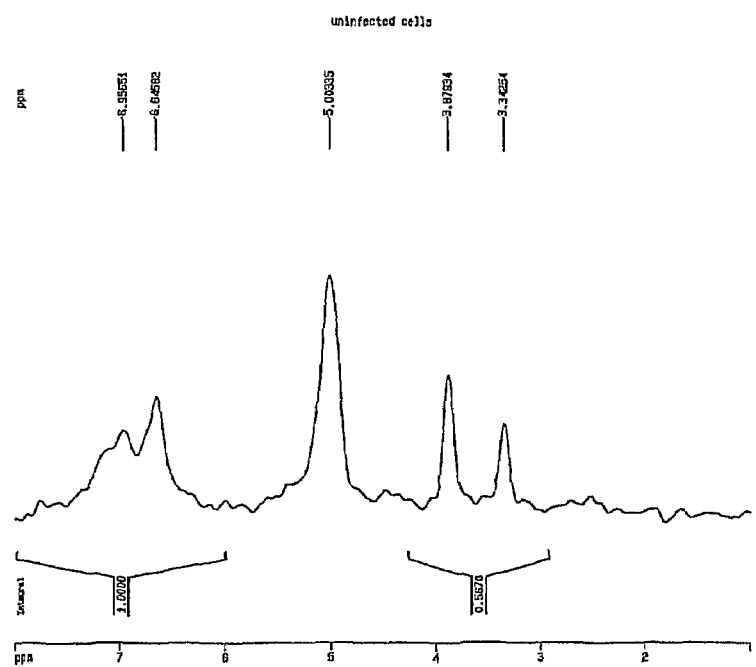
FIG. 3 shows expanded (Gaussian/Lorentzian multiplied) inorganic phosphate region (PME, PDE, and $P_i$) of perchloric acid extract of uninfected (A) and infected (B) human lymphocytes.
Figure 3:
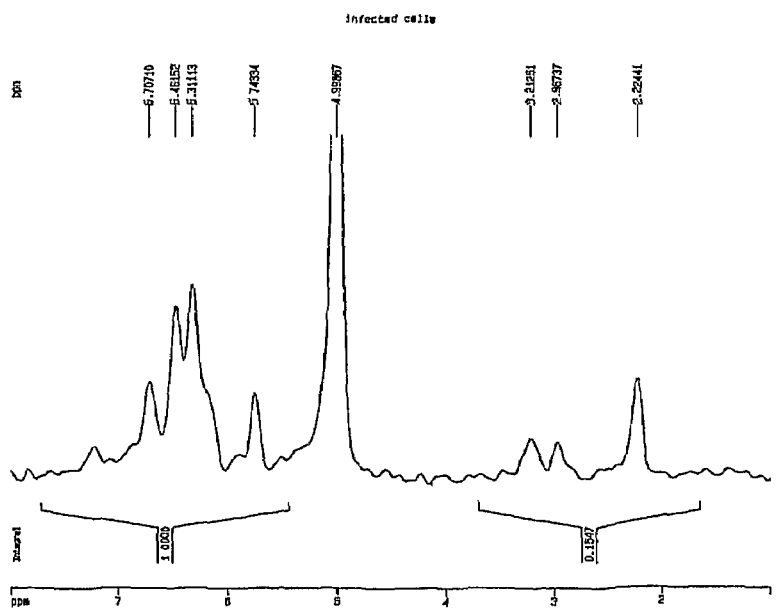

To enhance visualization of the PME and PDE peaks, the expanded region of interest (3.5-5.5 ppm) was processed using Gaussian/Lorentzian exponential line broadening as shown in FIG. 3. All components of the spectrum were very well resolved, and signal areas were easily found by integration of the curves using standard Bruker software. The calculated ratio of PDE to Pi was 0.77 in infected cells versus 1.50 in uninfected cells.

Figure 4:
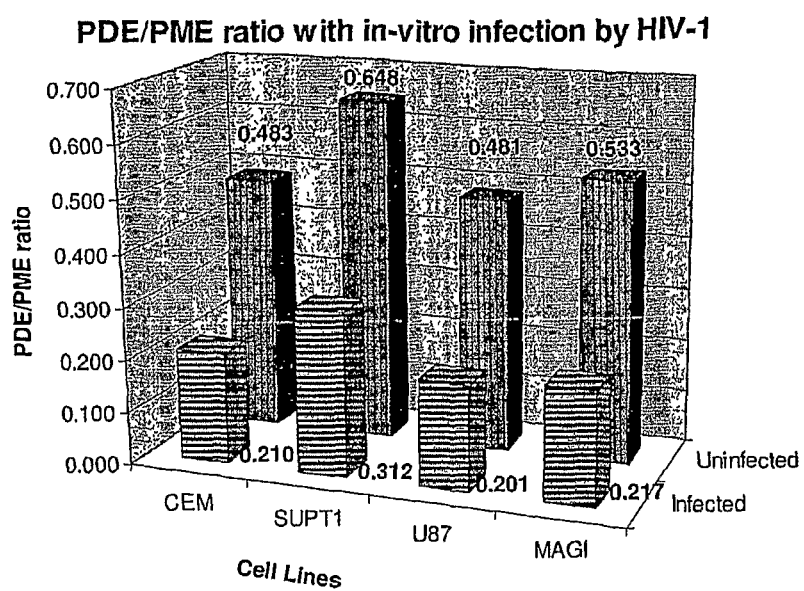
FIG. 4 shows PDE/PME ratio of cell lines (CEM, SUPT1, U87, MAGI) with and without in-vitro infection by HIV-1 (IIIB, 89.6).

Direct comparison of the PDE to PME levels is more illustrative of the impact of HIV-1 infection on membrane phospholipid composition. A breakdown of the PDE/PME ratio for the panel of cell lines studied is presented in FIG. 4. The PDE/PME ratio decreased from 2.1-2.5 fold in HIV-1 infected cell lines compared to uninfected control cells.

The results indicate essential differences in the low field portion of the $^{31}$P-NMR spectra from HIV-1 infected cells in comparison to uninfected cells. NMR visible PME and PDE are mainly involved in biochemical and biophysical processes related to cellular membranes. Results show that HIV-1 infection consistently alters membrane PDE and PME during the process of virus entry, integration and/or particle production. Therefore, PDE/PME ratio is predictive of the presence of HIV-1 in primary cells. The results from FIG. 4 demonstrate small variations in the basal PDE/PME ratio among different cell types; therefore, NMR analysis was first conducted on multiple isolates of uninfected PBMC to establish a baseline control for the PDE/PME ratio of uninfected primary lymphocytes as compared to cell lines.

Figure 5:
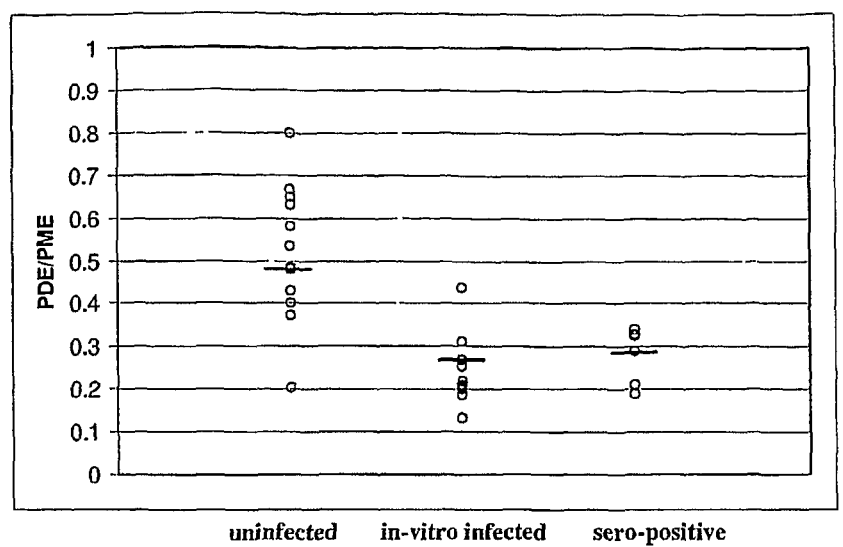
FIG. 5 PDE/PME ratio in human lymphocytes obtained from healthy donors (uninfected), from lymphocytes infected in-vitro with HIV-1 (in-vitro infected) and obtained from HIV-1 sero-positive patients (sero-positive).

As shown in FIG. 5, the mean PDE/PME ratio for 13 uninfected PBMC samples was 0.482±0.094. The result were then compared to the PDE/PME ratio for 13 independent PBMC isolates infected in vitro with HIV-1 IIIB. The mean PDE/PME ratio for in vitro infected PBMC was 0.203±0.076, and the PDE/PME ratio for all 13 samples fell below the 0.482 mean PDE/PME ratio seen for uninfected lymphocytes, with only one sample from the uninfected PBMC analysis fell below the 0.203 level. $^{31}$P-NMR spectra from six independent patient PBMC isolates were analyzed in a blinded fashion to determine whether the observation of reduced PDE/PME ratio was applicable to the analysis of lymphocytes obtained from HIV-1 sero-positive patients. The mean PDE/PME ratio for these samples was 0.270±0.07, and again all six samples fell below 0.482.

The foregoing has been a description of certain non-limiting preferred embodiments of the invention. Those of ordinary skill in the art will appreciate that various changes and modifications to this description may be made without departing from the spirit or scope of the present invention, as defined in the following claims.

What is claimed is:

1. A method for monitoring the severity of human immunodeficiency virus (HIV) infection in a subject, comprising:
   (1) obtaining a biological sample comprising lymphocytes from said subject;
   (2) measuring the concentration of phosphodiester (PDE) and the concentration of phosphomonoester (PME) in said biological sample;
   (3) computing an observed ratio of phosphodiester (PDE)/phosphomonoester (PME) from said concentrations;
   (4) comparing said observed ratio with a standard ratio obtained from the biological sample of a non-infected control subject; and
   (5) computing the difference between said observed ratio and standard ratio, wherein, the larger the difference between the observed ratio and the standard ratio, the more severe is the infection.

2. The method of claim 1, wherein said biological sample is plasma, saliva, urine, blood cell, lymphatic fluids, peripheral blood mononuclear cells (PBMC), thymocytes, or a combination thereof.

3. The method of claim 1, wherein said step of measuring the concentrations of PDE and PME comprises magnetic resonance imaging (MRI), nuclear magnetic resonance (NMR), high performance liquid chromatography (HPLC), gas chromatography(GC), mass spectrometry (MS), or a combination thereof.

4. The method of claim 1, wherein the HIV is HIV-1.

5. The method of claim 1, wherein said standard ratio is about 0.482 as measured by NMR of perchloric acid extracts from thymocytes.

* * * * *